(12) United States Patent
Beckner et al.

(10) Patent No.: US 10,471,276 B2
(45) Date of Patent: Nov. 12, 2019

(54) APPARATUS AND METHOD FOR PHOTONIC PHYSIOLOGICAL AND NEUROLOGICAL STIMULATION

(71) Applicant: The Regents of the University of California, Oakland, CA (US)

(72) Inventors: William Beckner, North Potomac, MD (US); John A. Ives, Alexandria, VA (US); Mark Bachman, Irvine, CA (US); Guann-Pyng Li, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/766,802

(22) PCT Filed: Oct. 7, 2016

(86) PCT No.: PCT/US2016/055965
§ 371 (c)(1),
(2) Date: Apr. 6, 2018

(87) PCT Pub. No.: WO2017/062752
PCT Pub. Date: Apr. 13, 2017

(65) Prior Publication Data
US 2018/0280721 A1 Oct. 4, 2018

Related U.S. Application Data

(60) Provisional application No. 62/238,650, filed on Oct. 7, 2015.

(51) Int. Cl.
*A61N 5/06* (2006.01)
*A61B 5/021* (2006.01)
(Continued)

(52) U.S. Cl.
CPC .......... *A61N 5/0619* (2013.01); *A61B 5/021* (2013.01); *A61B 5/02416* (2013.01);
(Continued)

(58) Field of Classification Search
CPC ... A61B 5/021; A61B 5/02416; A61B 5/0532; A61B 5/0816; A61B 5/4836;
(Continued)

(56) References Cited

U.S. PATENT DOCUMENTS 4,232,678 A 11/1980 Skovajsa
6,266,558 B1 7/2001 Gozani
(Continued)

FOREIGN PATENT DOCUMENTS

CN 295400 Y 12/2003
CN 101336863 1/2009
(Continued)

OTHER PUBLICATIONS

Written Opinion ISA/KR; PCT/US2016/055965; dated Jan. 10, 2017.
(Continued)

*Primary Examiner* — Aaron F Roane
(74) *Attorney, Agent, or Firm* — The Richards Law Firm LLC; William B. Richards, Esq.

(57) ABSTRACT

An apparatus and method utilizes photonics, particularly lasers, and biometric feedback for physiological and neurological stimulation. While many areas of the body are candidates, such laser stimulation is particularly directed to the outer ear. Lasers positioned over the ear stimulate targets on the outer ear for pain and stress management and regulation of the autonomic nervous system to affect symptoms and clinical conditions. Laser positioning, wavelength, aiming, focus, power, power density, timing, and sequencing are
(Continued)

managed and modified dynamically in real time to effect a personalized and effective treatment protocol.

10 Claims, 5 Drawing Sheets

(51) Int. Cl.
*A61B 5/024* (2006.01)
*A61B 5/053* (2006.01)
*A61B 5/08* (2006.01)
*A61B 5/00* (2006.01)
*A61N 5/067* (2006.01)

(52) U.S. Cl.
CPC .......... *A61B 5/0532* (2013.01); *A61B 5/0816* (2013.01); *A61B 5/4836* (2013.01); *A61N 5/0622* (2013.01); *A61N 2005/0605* (2013.01); *A61N 2005/067* (2013.01); *A61N 2005/0647* (2013.01)

(58) Field of Classification Search
CPC ................ A61N 5/0619; A61N 5/0622; A61N 2005/0605; A61N 2005/0647; A61N 2005/067; A61N 5/06; A61N 5/062; A61N 5/0624; A61N 5/0625; A61N 2005/0626; A61N 2005/0627; A61N 2005/0628; A61N 2005/0639; A61N 2005/0645
USPC ...................................................... 607/88, 89
See application file for complete search history.

(56) References Cited

U.S. PATENT DOCUMENTS

| | | | |
|---|---|---|---|
| 6,366,802 B1* | 4/2002 | Haber | A61N 5/0619 600/474 |
| 6,507,755 B1 | 1/2003 | Gozani | |
| 6,754,472 B1 | 6/2004 | Williams | |
| 7,179,278 B2 | 2/2007 | Schikora | |
| 8,043,348 B2 | 10/2011 | Weber | |
| 8,948,876 B2 | 2/2015 | Gozani | |
| 2003/0083720 A1 | 5/2003 | Peterson | |
| 2004/0092859 A1 | 5/2004 | Detlet | |
| 2005/0004633 A1 | 1/2005 | Weber | |
| 2005/0228463 A1 | 10/2005 | Mac | |
| 2006/0047324 A1* | 3/2006 | Tass | A61B 5/0482 607/45 |
| 2006/0178660 A1 | 8/2006 | Neher | |
| 2007/0023710 A1* | 2/2007 | Tom | A61L 2/10 250/504 R |
| 2007/0088386 A1 | 4/2007 | Babaev | |
| 2007/0129713 A1 | 6/2007 | Weber | |
| 2009/0118800 A1* | 5/2009 | Deisseroth | A61N 5/0603 607/92 |
| 2010/0049007 A1 | 2/2010 | Sterling | |
| 2012/0053648 A1 | 3/2012 | Neher | |
| 2013/0303838 A1 | 11/2013 | Ahn | |
| 2013/0331640 A1* | 12/2013 | Nabat | A61M 21/02 600/28 |
| 2014/0107493 A1 | 4/2014 | Yuen | |
| 2015/0032092 A1* | 1/2015 | Adanny | A61B 18/203 606/9 |
| 2015/0343189 A1 | 12/2015 | Ostrovsky | |

FOREIGN PATENT DOCUMENTS

| | | |
|---|---|---|
| CN | 102580255 | 7/2012 |
| CN | 203043347 | 7/2013 |
| CN | 103735407 | 4/2014 |
| CN | 204106867 | 1/2015 |
| EP | 1 841 377 | 10/2007 |
| HU | 227035 | 5/2010 |
| RU | 2 202 331 | 4/2003 |
| RU | 2 327 443 | 6/2008 |
| RU | 2 373 917 | 11/2009 |
| RU | 2 410 077 | 1/2011 |
| RU | 2 428 224 | 9/2011 |
| RU | 2 511 058 | 4/2014 |

OTHER PUBLICATIONS

Brittner; Acupuncture in Pediatrics; Curr Probl Pediatr Adolsec Health Care, Jun. 2016, 46:179-183 (1-18).
Hou; The History, Mechanism, and Clinical Application of Auricular Therapy in Traditional Chinese Medicine; Evidence-Based Complementary and Alternative Medicine, 2015 (1-29).
Hsiu; Differences in the beat-to-beat parameters of skin-surface pulsatile laser-Doppler waveforms between stroke and normal subjects; Clinical Hemorheology and Microcirculation, 58 (2014) 353-362 (2-18).
Raith; Laser Acupuncture for Neonatal Abstinence Syndrome: A Randomized Controlled Trial; Pediatrics, 136:5, Nov. 2015 (2-19).
Hsiu; Complexity analysis of beat-to-beat skin-surface laser-Doppler signals in diabetic subjects; Microvascular Research, 93 (2014) 9-13 (3-18).
Dong; Treatments for Shoulder Impingement Syndrome; Medicine, vol. 4, No. 10, 1-17, Mar. 2015 (3-29).
Thabit; Combined Central and Peripheral Stimulation for Treatment of Chronic Tinnitus: A Randomized Pilot Study; Neurorehabilitation and Neural Repair, 2015, vol. 29(3) 224-233 (4-29).
Litscher; Integrative Laser Medicine and High-Tech Acupuncture at the Medical University of Graz, Austria, Europe; Evidence-Based Complementary and Alternative Medicine, vol. 2012, Article ID 103109, 1-21 (5-18).
Seo; Acupuncture in subjects with cold hands sensation: study protocol for a randomized controlled trial; Trials Sep. 2014, 15:348 (5-29).
Gao; Sino-European Transcontinental Basic and Clinical High-Tech Acupuncture Studies-Part 3: Violet Laser Stimulation in Anesthetized Rats; Evidence-Based Complementary and Alternative Medicine, vol. 2012, Article ID 402590, 8 pages (6-18).
Garcia-Zalisnak; Ocular surface diseases and corneal refractive surgery; Curr Opin Ophthalmol Jul. 2014, 25:264-269 (6-29).
Litscher; Technical Parameters for Laser Acupuncture to Elicit Peripheral and Central Effects: State-of-the-Art and Short Guidelines Based on Results from Medical University of Graz, the German Academy of Acupuncture, and the Scientific Literature; Evidence-Based Complementary and Alternative Medicine, vol. 2012, Article ID 697096 (7-18).
Ferreira; Effect of laser acupuncture and auricular acupressure in a child with trismus as a sequela of medulloblastoma; Acupuncture in Medicine, Jan. 2014, 0:1-4 (7-29).
Komori; Microcirculatory Responses to Acupuncture Stimulation and Phototherapy; Pain Mechanisms vol. 108, No. 2, Feb. 2009, pp. 635-640 (8-18).
White; Acupuncture and related interventions for smoking cessation; The Cochrane Collaboration 2014, John Wiley & Sons, Ltd. (8-29).
Litscher; Effects of laserneedle stimulation in the external auditory meatus on brainstem and very early auditory evoked potentials in humans; Neurological Research (2006) 28:8, 837-840 (9-18).
Round; Auricular Acupuncture with Laser; Evidence-Based Complementary and Alternative Medicine vol. 2013, Article ID 984763 22 pages. (9-29).
Shen; Acupuncture for schizophrenia; Cochrane Database of Systematic Reviews 2014, Issue 10. Art. CD005475 (10-18).
Wang; ATP Release from MAST Cells by Physical Stimulation: A Putative Early Step in Activation of Acupuncture Points; Evidence-Based Complementary and Alternative Medicine, vol. 2013, Article ID 350949, 7 pages (10-29).
Litscher; Near-infrared spectroscopy for objectifying cerebral effects of needle and lasemeedle acupuncture; Spectroscopy 16 (2002) 335-342 (11-18).

(56) References Cited

OTHER PUBLICATIONS

Schlager; Auricular electroacupuncture reduces frequency and severity of Raynaud attacks; Wien Klin Wochenschr The Central European Journal of Medicine (2011) 123: 112-116 (11-29).

Miittal; Profulla Kumar Sen: His Contributions to Cardiovascular Surgery; Texas Heart Institute Journal (2002) (12-18).

Litscher; Changed Skin Blood Perfusion in the Fingertip Following Acupuncture Needle Introduction as Evaluated by Laser Doppler Perfusion Imaging; Lasers Med Sci 2002, 17:19-25 (13-18).

Rusy; Electroacupuncture Prophylaxis of Postoperative Nausea and Vomiting following Pediatric Tonsillectomy with or without Adenoidectomy; Anesthesiology 2002, 96:300-5; American Society of Anesthesiologists, Inc. Lippincott Williams & Wilkins, Inc. (14-18).

Kim; Effect by acupuncture on hypothalamic expression of maternally separated rats: proteomic approach; Neurological Research, 2010, vol. 32, Supplement 1, pp. 569-573; W.S. Maney & Son Ltd. (15-29).

Marovino; Laser Auriculotherapy As Part of the Nicotine Detoxification Process: Evaluation of 1280 Subjects and Theoretical Considerations of a Developing Model; American Journal of Acupuncture, vol. 22, No. 2, 1994; pp. 129-135 (16-18).

Shang; Prospective Tests on Biological Models of Acupuncture; eCAM 2009:6(1)31-39; Advance Access Publication Nov. 21, 2007 (16-29).

Rosted; A Protocol for Successful Treatment of Chronic Skin Diseases with Acupuncture; American Journal of Acupuncture, vol. 20, No. 4, 1992 pp. 321-326 (17-18).

Chou; Nonpharmacologic Therapies for Acute and Chronic Low Back Pain: A Review of the Evidence for an American Pain Society/American College of Physicians Clinical Practice Guideline; Annals of Internal Medicine 2007; vol. 147, No. 7:492-504 (18-29).

Siedentopf; Neural correlates of transmeatal cochlear laser (TCL) stimulation in healthy human subjects; ScienceDirect, Neuroscience Letters 411 (2007) 1890-193 (20-29).

White; Acupuncture and related interventions for smoking cessation; Cochrane Database of Systematic Reviews 2011, Issue 1.Art. No. CD0000009 (21-29).

D'Alberto; Auricular Acupuncture in the Treatment of Cocaine/Crack Abuse: A Review of the Efficacy, the Use of the National Acupuncture Detoxification Association Protocol, and the Selection of Sham Points; The Jouranal of Alternative and Complementary Medicine; vol. 10, No. 6, 2004, pp. 985-1000 (22-29).

Zalewska-Kaszubska; Use of low-energy laser as adjunct treatment of alcohol addiction; Lasers in Medical Science (2004) 19:100-104 (23-29).

Dent; Continuous PC6 wristband acupressure for relief of nausea and vomiting associated with acute myocardial Infarction: a partially randomised, placebo-controlled trial; Complementary Therapies in Medicine (2003), 11, 72-77; Elsevier Science Ltd. (24-29).

Trumpler; Acupuncture for Alcohol Withdrawal: A Randomized Controlled Trial; Alcohol and Alcoholism, vol. 38, Issue 4, Jul. 2003, pp. 369-375 (25-29).

Casale; Systemic Sclerosis (Scleroderma): An Integrated Challenge in Rehabilitation; Arch Phys Med Rehabil, vol. 78, Jul. 1997 (26-29).

Wesselmann; Effects of Q-Switched Nd:YAG Laser Irradiation on Neural Impulse Propagation: I. Spinal Cord; Physiol. Chem. Phys. & Med. NMR (1991) 23:67-80 (29-29).

Rom; Sensory stimulation for lowering intraocular pressure, improving blood flow to the optic nerve and neuroprotection in primary open-angle glaucoma; Acupuncture in Medicine (Dec. 2013) vol. 31, No. 4, pp. 416-421; BMJ Publishing Group, British Med. Assoc. House, Tavistock Square, London.

Szathmary; Use of laser radiation in the veterinary practice. Basic knowledge and report of cases; Magyar Allatorvosok Lapja, (Jun. 1996) vol. 51, No. 6, pp. 343-347; Springer Hungarica Kiado Kft, Wesselenyi U 28, H-1075 Budapest, Hungary.

Ostendorf; So-called "alternative" therapies in rheumatology and orthopaedics' Aktuelle Rheumatologie, (Mar. 1997) vol. 22, No. 2, pp. 75-80; Georg Thieme Verlag, Stuttgart, Germany.

Liu; An acupuncture meta-analysis for optic atrophy Seven randomized, controlled trials; Neural Regeneration Research, (Dec. 2009) vol. 4, No. 12, pp. 994-1001; Shenyang Editorial Dept. Neural Regeneration Res. Shenyand, Liaoning.

Zhao; Clinical effects of acupuncture therapy for vascular dementia; Neural Regeneration Research, (Jan. 25, 2011) vol. 6, No. 3, pp. 193-199; Shenyang Editorial Department Neural Regeneration Res., Shenyang, Liaoning.

* cited by examiner

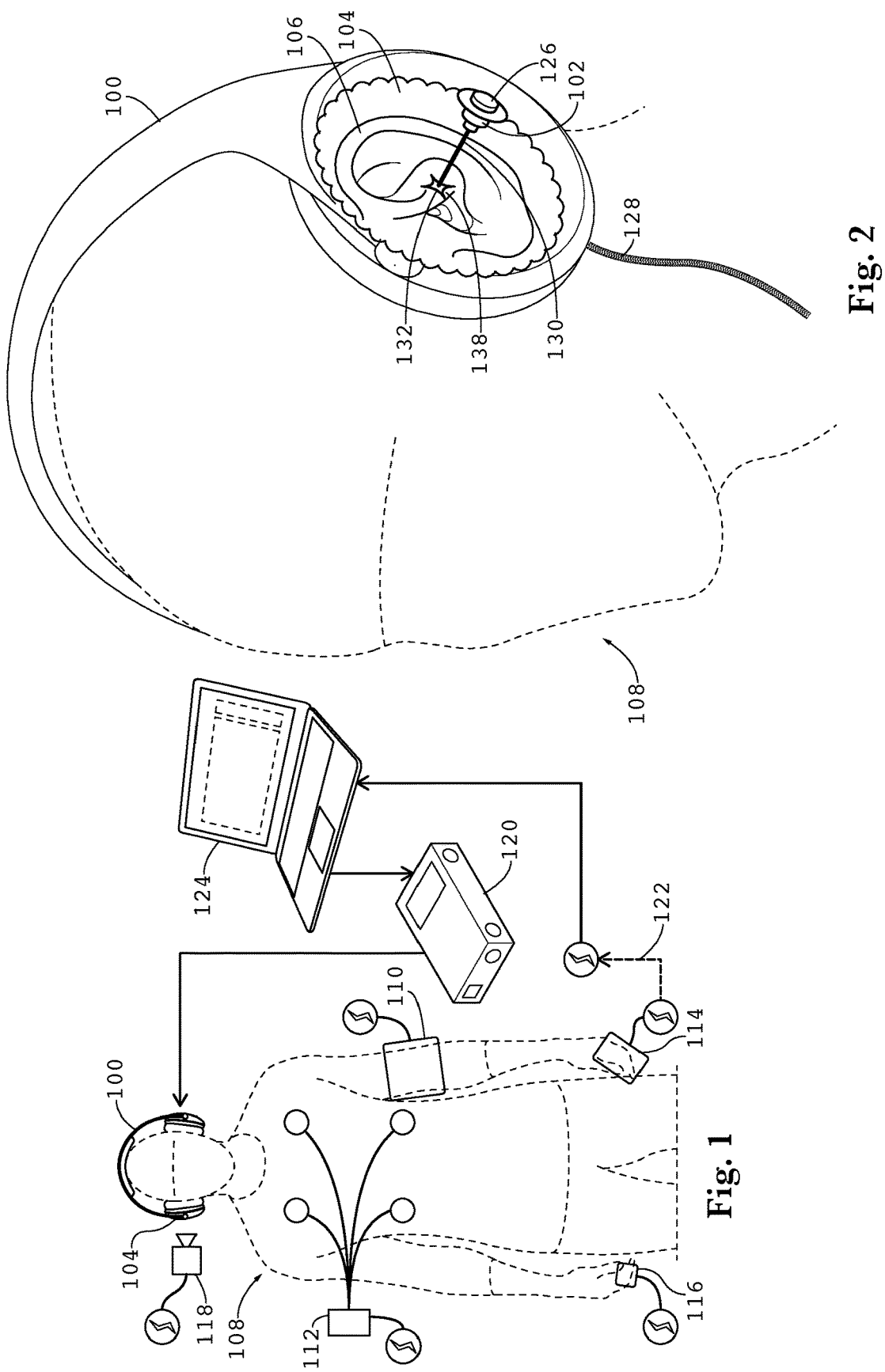

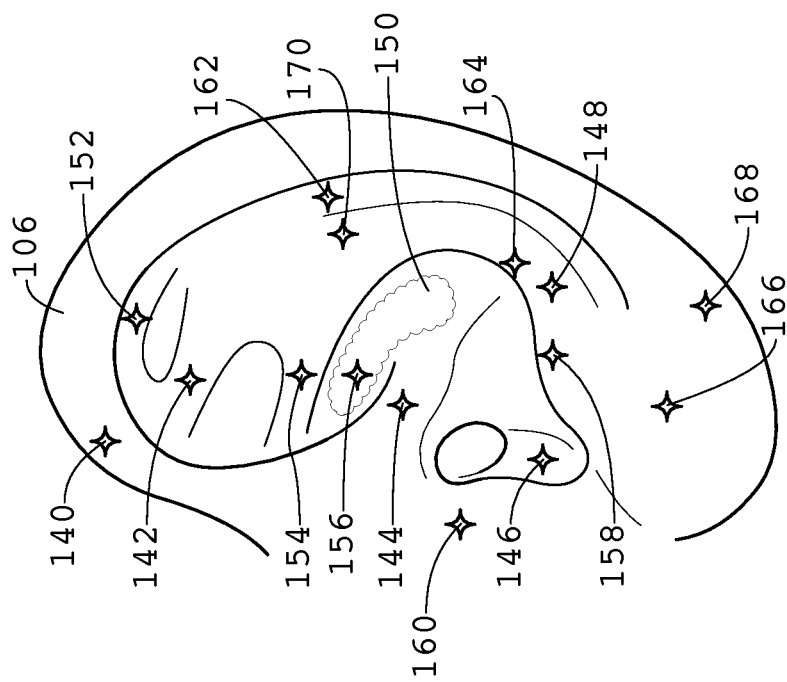
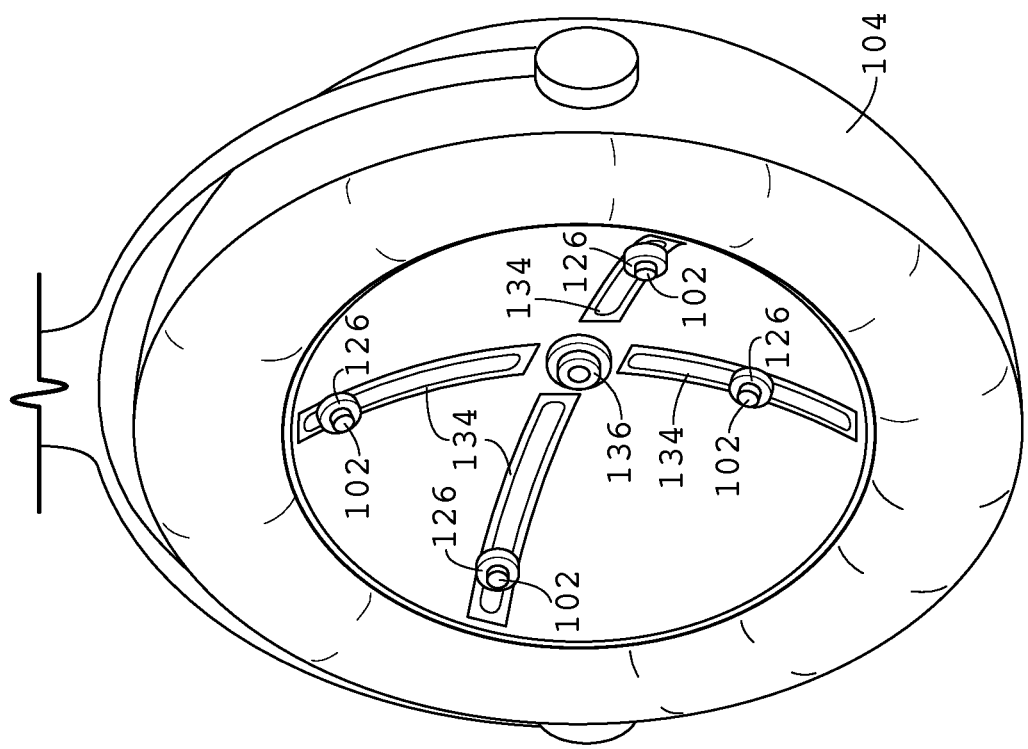
Fig. 4
Fig. 3

APPARATUS AND METHOD FOR PHOTONIC PHYSIOLOGICAL AND NEUROLOGICAL STIMULATION

CROSS-REFERENCE TO RELATED APPLICATION

This application is a national stage entry of International Application No. PCT/US2016/055965, entitled "Apparatus and Method for Photonic Physiological and Neurological Stimulation", filed in the RO/US on Oct. 7, 2016, which claims priority to U.S. Provisional Application No. 62/238,650, filed Oct. 7, 2015, entitled "Apparatus and Method for Physiological and Neuro-logical Therapy Using Photobiomodulation", which U.S. Application No. 62/238,650 is hereby incorporated by reference.

FEDERALLY-SPONSORED RESEARCH AND DEVELOPMENT

This invention was made with government support under Award Nos. W81XWH-08-01-0615, W81XWH-10-1-0938, and W81XWH-11-1-0538 awarded by United States Army Medical Research Acquisition Activity (USAMRAA). The government has certain rights in this invention.

JOINT RESEARCH AGREEMENT

This invention was made under a joint research agreement between Samueli Institute for Information Biology, Inc. and The Regents of the University of California, Inc., acting through the offices of The University of California, Irvine.

FIELD

This description relates generally to an apparatus and method for photonic physiological and neurological stimulation, particularly to the use of lasers and, optionally, light-emitting diodes (LEDs) to stimulate one or more points on the ear for pain and stress management and regulation of the autonomic system to affect symptoms and clinical conditions, and more particularly to such laser methods that record and store measurable physiological and neurological responses as biometric data, and more particularly to such methods that utilize biometric data to modify the laser therapy protocol, either dynamically in real time or later to modify the protocol in a future therapy session. Other applications include parts of the body other than the ear and to non-humans including, for example, horses and dogs.

BACKGROUND

Photonic stimulation using lasers involves the use of visible, near infrared, or ultraviolet light to induce a physiological or neurological response in living cells and tissue as a direct result of the absorbance of light by the living cells and tissue. With traditional applications, the light is imposed directly on the affected cells and tissue to treat localized pain, inflammation and edema, wounds, inflamed oral tissues, ulcerations, burns, dermatitis, and acne.

Classical acupuncture (literally, needle puncture) involves inserting very fine gauge needles, generally, 0.16-0.46 mm in diameter, into the body at selected sites, called acupuncture points. Stimulation of such sites by the needle, including those in the ear and hand, but including many other points, has indirect effects on other areas of the body. Treatments include pain management, including pain caused by headaches and migraines and osteoarthritis, nausea and vomiting, and stress management, including post-traumatic stress syndrome (PTSD).

Although fine gauge, acupuncture needles are invasive, in that they physically break the skin, and may not be suitable for those with a fear of needles, such as small children. In addition, classical needle acupuncture carries the risk of localized soreness, bleeding, and infections, including perichondritis and chondritis. Furthermore, acupuncture needles cannot be easily adjusted to optimize their effects. Finally, deaths due to complications following classical needle acupuncture treatment, although rare, have also been reported, albeit the result of improper technique or treatment, or both.

The use of lasers, to stimulate specific target points on the body, including classical acupuncture sites, particularly in the outer ear or hand, have recently been shown to produce physiological and neurological effects similar to classical needle acupuncture while being non-invasive. Such devices typically have wavelengths ranging from ultraviolet (less than ca. 390 nm) to infrared (up to about ca. 900 nm). Not only is wavelength responsible for the color of the light, it helps control the depth of penetration into the skin. Higher wavelengths, higher power, and power density provide greater depth of penetration. However, depth of penetration is also affected by the thickness and pigmentation of the skin.

Conventional methods of directing light sources include manually holding and manipulation or securing the light in a fixed position relative to the target point. Such protocols can be inconvenient for operation and may cause the positioning of the light beam to become unstable. Further, no allowance is made to simultaneously and independently position and control multiple light sources.

Thus, there is a need for light-based physiological and neurological stimulation that provides one or more stable, controller-directed light sources, such as lasers and LEDs, to stimulate specific points on the body, particularly on the outer ear, utilizing physiological and neurological feedback for dynamic, real-time modification of the protocol.

BRIEF SUMMARY OF THE INVENTION

The outer ear is innervated by spinal and cranial nerves. The facial nerve is responsible for the motoric innervation of the outer ear muscle, and, while not wishing to be bound by any particular theory, it is theorized that stimulation of points on the auricle stimulates the vagal nerve which carries the parasympathetic fibers both to the organs of the body and to the brain. Much, if not all, of the parasympathetic system is managed through a complex and still-not-completely-understood system of controls and feedbacks carried by the vagal nerve. Again, not wishing to be bound by any particular theory, it is theorized that there is interaction and stimulation of this part of the nervous system. Furthermore, the branch of the trigeminal nerve which carries the sympathetic fibers to the reticular formation where the information is distributed to the corresponding brain structures also run through the outer ear. Again, not wishing to be bound by any particular theory, a possible mechanism includes photon absorption by cytochrome-c-oxidase, the terminal enzyme in the mitochondrial respiratory chain that catalyzes the reduction of oxygen for energy metabolism. Stimulation of this mitochondrial enzyme may result in increased metabolic energy to the biosystems of which it is a part.

Disclosed is an apparatus and method for simultaneously and independently controlling and directing multiple light sources, exemplarily, laser light, to stimulate target points, particularly on the outer ear. Such control and direction may be effected according to a therapeutic protocol, including the ability to record and utilize measured physiological and neurological responses to control and direct the laser treatment dynamically and in real time to produce a personalized and effective treatment protocol or to track treatment over time. Laser stimulation may be directed at multiple target points on the ear simultaneously, or in a rapid, complex order. Treatment may be personalized during a single session or over the course of a number of sessions based upon measured data. Treatments may include pain and stress management, cardiovascular regulation, wound healing, treatment of cognitive disorders, depression, hypertension, appetite suppression, and addictive behavior such as alcoholism and smoking. Of particular interest is the treatment of members of the armed forces to assist with pain management and to enhance the resilience and fitness domains (e.g., physical training, nutrition, social relationships, sleep, and unit cohesion).

In one embodiment, an apparatus provides cups or other laser mounting and positioning elements whereby one or more lasers can be directed to a point on the ear and controlled for the purpose of producing a physiological or neurological response. Optionally, additional features may be included, such as the ability to control the lasers according to a pre-defined protocol through, for example, a software interface, a video system for viewing the ear and beam spots, a sound system for delivering sound or music, and one or more physiological or neurological monitors to complete feedback control.

In a further embodiment, a head-worn apparatus comprises ear modules such as earphones or earmuffs that include one or more lasers within each ear covering.

In a further embodiment, a head-worn apparatus comprises a helmet-like structure which houses laser mounting and positioning elements whereby one or more lasers can be directed to a point on the ear and controlled for the purpose of producing a physiological or neurological response.

In a further embodiment, driver circuitry is included to control the output intensity of the lasers.

In a further embodiment, the direction and/or focus of each laser is adjustable to ensure proper direction of the desired laser energy to the appropriate locations on the ear.

In a further embodiment, a combination of two or more wavelengths are simultaneously focused on individual target points to stimulate multiple tissue layers to specific depths, thereby simultaneously effecting treatment of multiple symptoms. Other variables include input power to each laser, area of illumination, area of stimulation, distance to skin surface, angle relative to skin surface, and frequency and duration of stimulation.

In a further embodiment, power is provided to the components of the apparatus, either on the apparatus or through an external power line.

In a further embodiment, one or more video cameras are included for monitoring the location of the beam spots.

In a further embodiment, the lasers are managed by a controller. The controller may be placed within the head-worn apparatus or may be external to the apparatus and communicate by way of wired or wireless telemetry. The controller may store one or more predefined treatment protocols.

In a further embodiment, physiological and neurological sensors such as heart rate and blood pressure monitors and brain scan measurements provide feedback information for adjusting the laser therapy protocol to the needs of the specific person.

In a further embodiment, an apparatus for laser light physiological and neurological stimulation of target points on the outer ear of a subject is provided. The apparatus comprises two cup-shaped housings, each housing adapted to fit the concave portion of the housing over an ear of the subject, a plurality of laser lights positioned at least partially within the concave portion of each housing, each laser light mounted to be aimed and focused on a target point on the outer ear, a video camera positioned at least partially within the concave portion of each housing, each video camera mounted to view the outer ear and a beam spot produced by each laser light, a sensor, the sensor in sensory communication with the subject, the sensor adapted to sense at least one physiological or neurological status of the subject, the sensor further adapted to output the at least one physiological or neurological status, a driver, the driver operably connected to each laser light, the driver capable of powering and controlling the laser lights and the video camera, and a command module, the command module operably connected to the driver and operably connected to the sensor, the command module further operably connected to the video camera, the command module adapted to: (a) control: (i) at least one performance variable of each laser light, the performance variables selected from the group consisting of light wavelength, power, power density, voltage, current, pulse pattern, pulse frequency, beam spot diameter, angle of incidence, and combinations thereof, (ii) the position of each laser light within the housing, and (iii) the focus of each laser light on the outer ear, (b) receive at least one status output from the sensor, (c) adjust at least one performance variable of at least one laser light, (d) subsequent to adjusting at least one performance variable (c), evaluate any change in the status output, (e) subsequent to evaluating any change in the status output (d), determine if the status output is optimized, and (e) adjust at least one variable of at least one laser light (c) if the status output is not optimized.

In a further embodiment, a method is provided for physiologically and neurologically stimulating target points on the outer ear of a subject, the method comprises the steps of: (a) mounting the concave portion of a cup-shaped housing over each ear of the subject, each housing comprising: a plurality of laser lights positioned at least partially within the concave portion, each laser light mounted to be aimed and focused on a target point on the outer ear, each laser light in operable communication with a driver, and a video camera positioned at least partially within the concave portion, each video camera mounted to view the outer ear and a beam spot produced by each laser light, the video camera in operable communication with the driver and in operable communication with a command module, (b) placing at least one sensor in sensory communication with the subject, the sensor in operable communication with the command module, the sensor adapted to sense at least one physiological or neurological status of the subject, the sensor further adapted to output the at least one physiological or neurological status to the command module, (c) initiating the command module to energize the laser lights at minimum power and beam spot onto the surface of the outer ear, (c) initiating the command module to adjust laser targeting onto initial target points, (e) initiating the command module to adjust at least one performance variable of at least one laser light, (f) initiating the command module to compare a sensor output from before Step (e) to the sensor output from after Step (e), and (g)

initiating the command module to determine if an optimum level of sensor output has been achieved.

In a further embodiment, an apparatus is provided for photonic physiological stimulation of at least one target point on a subject, the apparatus comprises a housing adapted to be positioned over the at least one target point, at least one light source selected from the group consisting of laser, light-emitting diode, and combinations thereof, the at least one light source positioned on the housing whereby light from the light source is focusable onto the at least one target point, at least one sensor, the at least one sensor in sensory communication with the subject, the sensor adapted to sense at least one physiological or neurological status of the subject, the sensor further adapted to output the at least one physiological or neurological status, a driver, the driver operably connected to the at least one light source, the driver capable of powering and controlling the at least one light source; and a command module, the command module operably connected to the driver and operably connected to the sensor, the command module adapted to (a) control at least one performance variable of the at least one light source, the at least one performance variable selected from the group consisting of light wavelength, power, power density, voltage, current, pulse pattern, pulse frequency, beam spot diameter, angle of incidence, and combinations thereof, (b) receive at least one status output from the sensor, (c) adjust at least one performance variable of at least one laser light, (d) subsequent to adjusting at least one performance variable (c), evaluate any change in the status output, (d) subsequent to evaluating any change in the status output (d), determine if the status output is optimized, and (e) adjust at least one performance variable of at least one laser light (c) if the status output is not optimized.

In a further embodiment, a further housing is provided, each housing being cup-shaped and each housing being adapted to fit the concave portion of the housing over an ear of the subject.

In a further embodiment, at least one of the light sources is a laser.

In a further embodiment, the laser is capable of emitting light having a frequency of between about 390 nm and about 700 nm.

In a further embodiment, the at least one physiological or neurological status is selected from the group consisting of blood pressure, blood flow, pulse, heart rate variability, blood oxygen saturation, electromyocardiographic response, respiration rate, respiration pattern, galvanic skin response, pupil dilation, trabecular-ciliary process distance, magnetic resonance imaging, brain waves, physical movements, muscle tension, self reporting, and combinations thereof.

In a further embodiment, the at least one performance variable is selected from the group consisting of light wavelength, power, power density, voltage, current, pulse pattern, pulse frequency, beam spot diameter, angle of incidence, and combinations thereof.

In a further embodiment, a method is provided for the photonic physiological stimulation of at least one target point on a subject, comprising the steps of (a) placing a housing over at least one target point, the housing comprising at least one light source selected from the group consisting of laser, light-emitting diode, and combinations thereof, the light source positioned on the housing whereby light from the light source is focusable onto the target point, (b) placing at least one sensor in sensory communication with the subject, the sensor adapted to sense at least one physiological or neurological status of the subject, the sensor further adapted to output the status, (c) energizing the light source at the target point at minimum power and beam spot, (d) noting the sensor output, (e) modifying at least one performance variable of the light source, (f) noting the sensor output, (g) comparing the sensor output noted in Step (d) with the sensor output noted in Step (e), (h) returning to Step (e) if the sensor output noted in Step (f) has not reached an optimum.

In a further embodiment, the physiological or neurological status is selected from the group consisting of blood pressure, blood flow, pulse, heart rate variability, blood oxygen saturation, electromyocardiographic response, respiration rate, respiration pattern, galvanic skin response, pupil dilation, trabecular-ciliary process distance, magnetic resonance imaging, brain waves, physical movements, muscle tension, self reporting, and combinations thereof.

In a further embodiment, the at least one performance variable is selected from the group consisting of light wavelength, power, power density, voltage, current, pulse pattern, pulse frequency, beam spot diameter, angle of incidence, and combinations thereof.

BRIEF DESCRIPTION OF THE SEVERAL FIGURES

The invention will be more readily understood by reference to the accompanying figures. The figures are incorporated in, and constitute a part of, this specification, illustrate several embodiments consistent with the invention and, together with the description, serve to explain the principles of the invention. For purposes of illustration, drawings may not be to scale.

FIG. 1 shows an overview of an embodiment of the present invention, including a headset with multiple light sources, physiological and neurological feedback sensors exemplified by a blood pressure sensor, heart- and respiration-related sensors, a galvanic skin response sensor, a pulse oximeter, ocular-related sensors, a controller, and a command module.

FIG. 2 shows, first, a laser-based apparatus with ear modules for housing lasers, driver electronics to power and control the lasers, and related components mounted on the head of a subject and second, a partial cutaway showing the laser directed onto the outer ear and also showing a fiducial mark placed on the ear.

FIG. 3 shows a view from the ear of an embodiment using tracks to position the light sources and an imaging camera.

FIG. 4 shows the contours of the outer ear and noting preferred general target points for photonic stimulation.

Figure 5A:
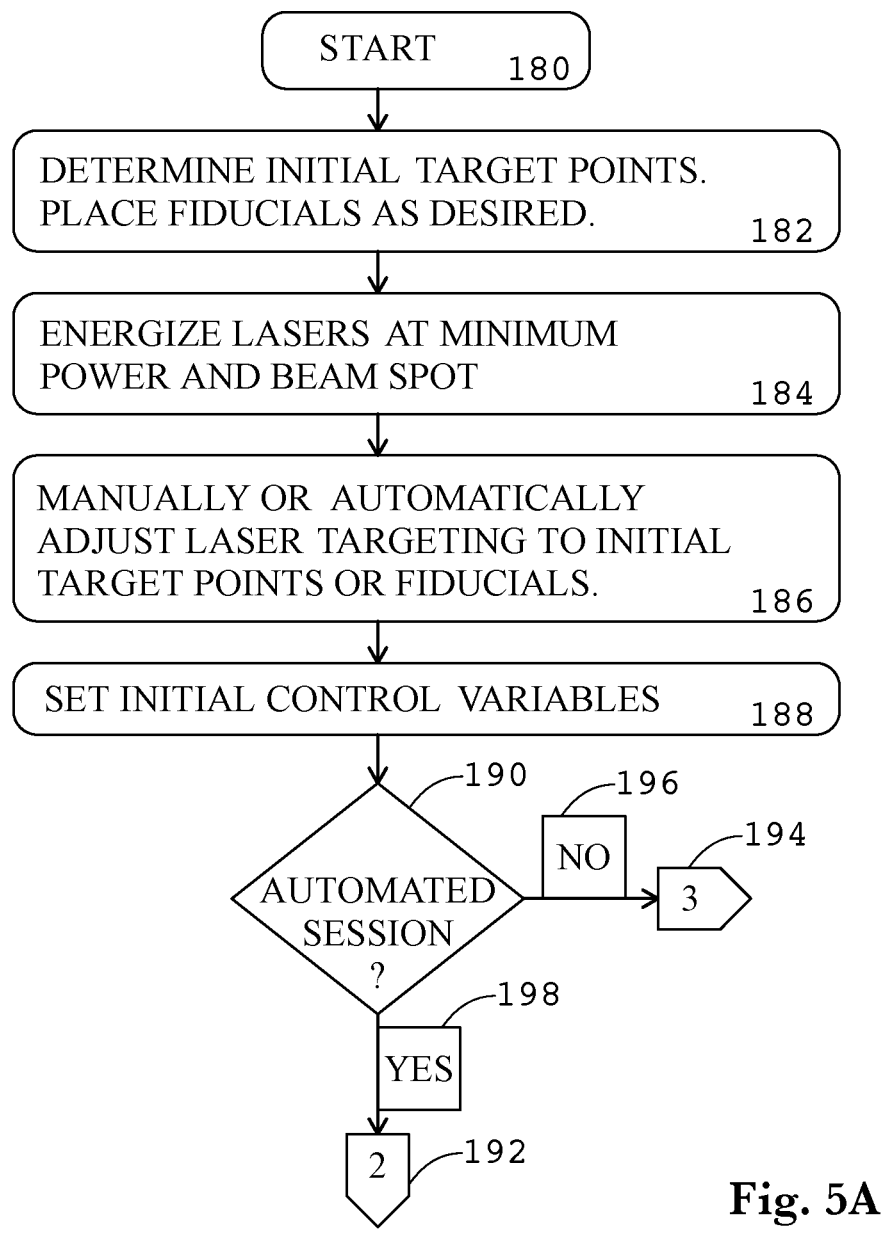
FIGS. 5A and 5B show an exemplary overall system flowchart of a photonic stimulation session.

In describing the various embodiments of the invention, specific terminology will be resorted to for the sake of clarity. However, it is not intended that the invention be limited to the specific terms so selected and it is to be understood that each specific term includes all technical equivalents which operate in a similar manner to accomplish a similar purpose.

DETAILED DESCRIPTION

FIG. 1 illustrates the various components of an exemplary overall system for photonic physiological and neurological stimulation. Shown are a headset 100 which includes one or more lasers 102 (not shown in FIG. 1, but see FIGS. 2 and 3) in each cup-like housing 104 covering the ears 106 (not shown in FIG. 1, but see FIG. 2) to deliver photonic stimulation to the subject 108. To provide physiological and neurological feedback, various monitors may be used, either alone or in combination, exemplarily shown as a blood pressure monitor 110, heart- and respiration-related monitors 112, a galvanic skin response (GSR) monitor 114, a pulse oximeter monitor 116, and ocular-related monitors 118. Although not specifically shown, such feedback may also include pulse, respiration rate and pattern, heart rate variability (HRV), pupil dilation, trabecular-ciliary process distance (TVPD), electroencephalogram (EEG), electromyocardiographic response (EMG), magnetic resonance imaging (MRI), movements, muscle tension, and self reporting. A driver 120 communicates, either wirelessly or via hardwired connections 122, with the various components in the headset 100, including the lasers 102, and a command module 124, which command module 124 also communicates, either wirelessly or via hardwired connections 122, with feedback monitors 110, 112, 114, 118. Each element of the system shown in FIG. 1 is described in more detail below. While not shown, a laser 102 mounted on a hand wand could also be used to reach other parts of the subject 108.

FIG. 2 shows a head-mounted apparatus 100 which includes cup-like housings 104 adapted to position one or more lasers or light sources 102 over one or both ears 106 of a subject 108. The lasers 102 are operably connected to the housing 104, optionally by one or more laser mounts 126. Additionally, driver electronics (not shown) may be operably connected to the laser 102 through the laser mount 126. Also shown is a cord 128 connecting the head-mounted apparatus 100 and the components associated with the housing 104 with the driver 120 and power supply (not shown). Alternatively, the power supply and a small driver 120 may be placed onboard and the driver 120 communicate wirelessly 122. While not shown, a sound system may be employed to provide voice contact with the subject 108 and/or to provide music.

Shown in cutaway in FIG. 2 is the headset 100 and the housing 104 over the ear, and including the laser mount 126 and the laser 102, and showing a laser beam 130 directed to a target point 132 on the ear 106 (also identified with a fiducial mark 138). While power may be supplied onboard and controls managed wirelessly, FIG. 2 shows a hardwired connector cord 128. Reference is also made to FIG. 3 which shows an embodiment with multiple laser mounts 126 and lasers 102. As will be appreciated by one skilled in the relevant art, such multiple lasers 102, may be employed under various protocols.

The headset 100 may be of any suitable design that enables the housings 104 to position the lasers 102 over the ear 106. The housings 104 may be solid, cup-like devices as shown, may be perforated to provide air circulation, may be just frames, or may comprise track-like structures 134 (as shown in FIG. 3 and described in related text) to which are operably connected one or more lasers 102 and laser mounts 126. With a track-like structure of FIG. 3, the lasers 102 may be movably coupled to the tracks 134 and allowed to slide along the tracks 134 to assist in directing the laser beam 130 (FIG. 2). Such an arrangement could also facilitate positioning the laser 102 directly over a target point 132 to allow for the beam 130 to strike normal to the surface of the ear 106.

The light sources, preferably lasers 102, generally operate in the visible range of about 390 to about 700 nm, but may also operate in the ultraviolet range below about 390 nm or in the infrared up to about 900 nm. Turning now to Tables 1-3, typical visible range wavelengths include blue (e.g., about 405 nm up to about 475 nm), green (532 nm), and red (e.g., 650 nm).

TABLE 1

| | |
|---|---|
| Model | Red-50 mW 650ML(120)-50-1242-XL650 nm |
| Output Power | 50 mW |
| Wavelength | 650 nm |
| Working Voltage | 3~6 V |
| Working Current | No |
| Working Temperature | 15-35 deg. C. |
| Duty Cycle | No |
| TTL | No |
| Laser Shape | Line |
| Divergence | Length 1-3 m at 1 m; Width <2 mm at 1 m |
| Focusable | Yes |
| Material and Color | Metal |
| LD | No |
| Lens | Glass |
| Waterproof | No |
| Heatsink | No |
| Memory | No |
| Dimensions | 12.5 mm × 12.5 mm × 42 mm |
| Working Life | No |
| Package | No |

TABLE 2

| | |
|---|---|
| Model | Blue-Violet-405 nm 2000 mW 405MD-2o00-1242-wA-XL |
| Output Power | 200 mW |
| Wavelength | 405 nm |
| Working Voltage | 3~5 V |
| Working Temperature | 10~40 deg. C. |
| Duty Cycle | No |
| TTL | No |
| Laser Shape | dot |
| Waterproof | No |
| Heatsink | No |
| Memory | No |
| Dimensions | 14.5*45 mm |
| Working Life | No |
| Package | 1 × 405 nm 2000 m@laser dot module w/adapter |

TABLE 3

| | |
|---|---|
| Model | 532 nm Green = 20 mW YH-N-20 |
| Output Power | 20 mW |
| Wavelength | 532 nm |
| Working Voltage | 2.9-3 V |
| Working Current | <280 mA |
| Working Temperature | 15~35 deg. C. |
| Duty Cycle | 40 secs. ON, 20 secs. OFF |
| TTL | No |
| Laser Shape | dot |
| Divergence | <25 × 25 mm at 15 m |
| Focusable | N/A |
| Material and Color | Brass |
| LD | No |
| Lens | Glass |
| Waterproof | No |
| Heatsink | No |
| Memory | No |
| Dimensions | 13 × (34 + 16) mm |
| Working Life | No |
| Package | No |

Sources include Laserlands, a professional laser manufacturer, retailer, and distributor based in Wuhan City, China. Also suitable are lasers 102 of the vertical-cavity surface-emitting type (VCSEL). VCSELs emit a beam 130 vertically from their emitting surface, thus making them easier to aim, facilitating a beam 130 that is normal to the surface at the target point 132, and enabling a tighter beam spot. Beam spots on the order of 1 mm in diameter are preferred and preferably the focal length of the beam 130 can be adjusted via a focusing bezel (not shown) to adjust the size of the beam spot. Power is generally in the range of about 5 mW to about 500 mW, with a preferred range of between about 5 mW and 50 mW. Power densities can range as low as 5 mW/cm$^2$ or less and as high as 500 mW/cm$^2$. Different wavelengths result in different action on the tissues (e.g., heating, ionization, excitation, photochemical response). And, since light absorption is wavelength dependent, the wavelength also affects the depth of penetration of the light, but is generally about 1 mm from the surface. Lasers 102 which are tunable by varying the wavelengths are also possible.

Looking again at FIG. 2 (and also FIG. 3), laser mounts 126 and driver electronics (not shown) may be adapted to provide a full range of functionality to the lasers 102. First, it is useful for the lasers 102 to be easily mounted and changed. For example, attachment of the lasers 102 to mounts 126 may be magnetic or with a snap fit, friction fit, turn-and-lock, or locking wheel. The lasers 102 may also be clipped or screwed into the mounts 126. Further mounting options include a ball-shaped base for the laser 102 to enable free movement to be angled up to 20 degrees or more from center on a 360-degree arc. As will be appreciated by those skilled in the relevant art, other mountings and attachments are possible within the bounds and spirit of the invention.

Driver electronics enable the lasers 102 to be fully adjustable and controllable. First, the lasers 102 can be moved to position each laser 102 directly over a target point 132 (see FIGS. 2 and 4), via tracks 134 (best seen in FIG. 3), for example, to enable the beam 130 to be directed normal to the surface as discussed above. Second, the lasers 102 may be angled along their axis to change the point to which the beam is directed. This provides further flexibility in directing the laser 102 onto the desired target point 132.

In addition to positioning and directing the lasers 102, driver electronics may also adjust which lasers 102 are activated, for example, depending upon the desired effects, which wavelengths are desired. Further, other operational variables of the lasers 102 such as total power and total power density of selected lasers 102 may be manipulated. Depending upon the protocol, power to the lasers 102 may be increased or decreased and, with selected lasers 102, the diameter of the beam 130 striking the target point 132 can be adjusted. (See Table 4.)

Power to the lasers 102, controlled by varying the current, for example, may follow specific time patterns, depending upon the session protocol. Exemplary profiles include a constant, plateau-like profile and a pulsed profile. Pulse rates can range from 1 Hz to 200 Hz. Other profiles are also contemplated, such as random, sinusoidal, and sawtooth. (See Table 4.)

Turning again to FIG. 3, an internal view of a cup-like housing 104 is shown, including lasers 102, positioning structures (not shown), such as actuators, including piezoelectric motors, linear electromagnetic actuators (LEA), stepper motors, and voice coil motors (VCM), tracks 134, and an imaging camera 136. The imaging camera 136 need not be limited to the visual spectrum, but may also be able to image wavelengths in the ultraviolet and/or infrared spectrum. As discussed above, the positioning structures and tracks 134 position the laser 102 and direct the laser beam 130 (FIG. 2) toward the target point 132 (FIG. 2). In an exemplary embodiment, the imaging camera 136 facilitates directing the laser beam 130 to the target point 132. The camera 136 captures the contours of the ear 106 (FIGS. 2 and 4) and identifies target points 132 (FIGS. 2 and 4). Alternatively, as seen in FIG. 2, the camera 136 can identify fiducial marks 138. Once the target point 132 is identified, the laser 102 may be properly positioned and the laser beam 102 (FIG. 2) directed to the target point 132 (FIGS. 2 and 4).

Turning now to FIGS. 2-4 and 6, in one phase of operation, the imaging camera 136 captures an image of the contours of the ear 106. The image may then be compared with a target point 132 based on the contours of the ear 106. Alternatively, if a fiducial mark 138 has been placed onto the ear 106, the camera 136 can recognize the fiducial mark 138 as the desired target point 132. By comparing the focus of the laser beam 130 with the desired target point 132, the laser beam 130 may be accurately directed to the target point 132. Further operations are discussed below and with reference to FIGS. 5 and 6.

Turning now to FIG. 4, while classical acupuncture identifies over 200 acupuncture sites in the ear 106, FIG. 4 first identifies five of the preferred target points 140, 142, 144, 146, 148 for stimulation by laser beams 102. They are Omega 2 140, located on the internal body of the helix, Shen Men 142, located at the apex of the triangular fossa, Point Zero 144, located at the junction of the conchal ridge and the ascending helix, Cingulate Gyms 146, located at the intertragic notch, and Thalamus 148, located at the base of the wall of the antitragus, adjacent to the inferior concha. These sites may be used as target points 132. Knowing the location of these sites on the anatomical topography of the ear 106 enables the laser beam 130 to be positioned and directed with the assistance of the imaging camera 136 (FIG. 3). Other sites on the ear 106 include Point O' 160, the trigeminal zone 168, and stellate ganglion 170. Anatomical sites include the thumb 152, sympathetic 154, the liver 156, the hypothalamus 158, the shoulder 162, the maxilla 164, and the eye 166.

There are many physiological and neurological sensors which may be used to provide biometric feedback data which may be used either dynamically in real time, or later to modify the protocol in a future session. Such data include blood pressure, pulse, blood flow, heart rate variability (HRV), blood oxygen saturation, electroencephalogram (EEG), electromyocardiographic response (EMG), respiration rate, respiration pattern, galvanic skin response (GSR), pupil dilation, trabecular-ciliary process distance (TCPD), magnetic resonance imaging (MRI), movements, muscle tension, and self reporting. By providing real-time feedback of selected physiological and neurological measurements, the command module 124 in cooperation with the driver 120 (FIG. 1) can modify the laser protocol accordingly to optimize the protocol. Table 4 below is an exemplary list of dependent and independent variable which can be used during a session.

TABLE 4

| Dependent Variables | Independent/Control Variables |
| --- | --- |
| blood pressure (e.g., related to stress) | light wavelength (e.g., near infrared, ultraviolet, blue, green)* |
| blood flow | |
| pulse (e.g., related to stress and alertness) | |
| heart rate variability (HRV) (e.g., related to stress) | power density (e.g., joules/cm$^2$)* |
| | light beam diameter* |
| | light angle* |
| blood oxygen saturation | voltage* |
| electromyocardiographic response (EMG) | current* |
| | shape |
| respiration rate (e.g., related to stress) | target point |
| respiration pattern | pulse pattern (e.g., sinusoidal, saw-tooth)* |
| galvanic skin response (GSR) | |

TABLE 4-continued

| Dependent Variables | Independent/Control Variables |
|---|---|
| pupil dilation (e.g., related to relaxation, stress and alertness) | pulse frequency* |
| trabecular-ciliary process distance (TCPD) | beam spot diameter* |
| magnetic resonance imaging (MRI) | angle of incidence* |
| brain waves (e.g., EEG) | beam combination(s) |
| movements | order of stimulation |
| body temperature (e.g., core and peripheral) | |
| muscle tension (e.g., related to relaxation and stress) | |
| self reporting (e.g., pain, sense of well-being) | |

*Also known as performance variables.

Figure 5B:
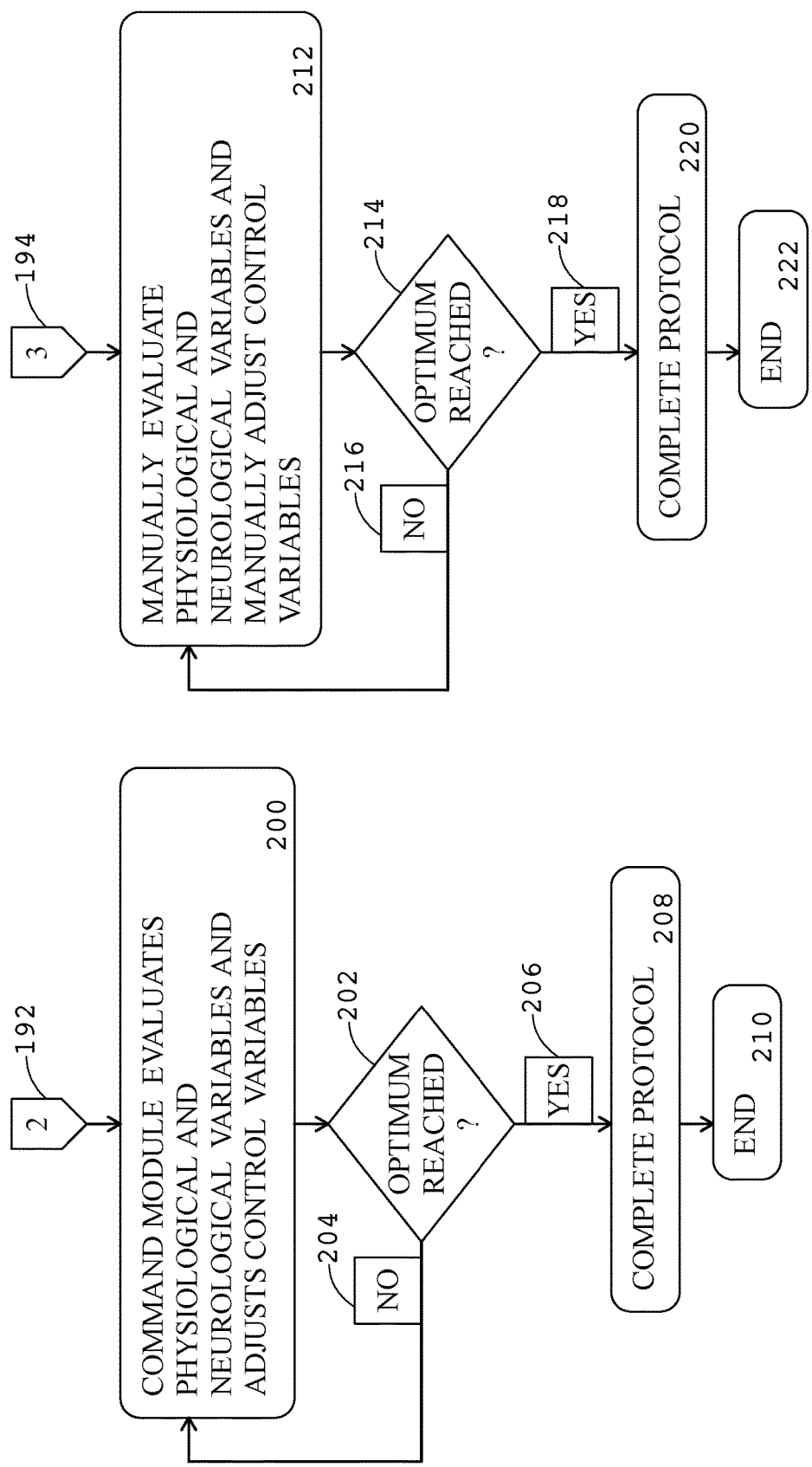

An exemplary overall system flowchart of a session is shown in FIGS. 5A and 5B. Specific elements referred to in this discussion of FIGS. 5A and 5B are shown in other figures and described in related text. A session may begin at Start 180. First, Determine initial target points.—and—Place fiducial marks as desired 182. Next, Energize lasers at minimum power and beam spot 184. Next, Manually or automatically adjust laser targeting to initial target points or fiducial marks 186 then Set initial control variables 188. If Automated session? 190 is Yes 198, go to Reference 2 192, if No 196, go to Reference 3 194. At Reference 2 192, Command module evaluates physiological and neurological variables and adjusts control variables 200. (See FIG. 1 and Table 4.) Adjustments may be based upon, for example, perturbing an Independent/Control Variable (Table 4) and check the effects on related Dependent Variables. If Optimum reached? 202 is No 204, loop back to Command module evaluates physiological and neurological variables and adjusts control variables 200. If Optimum reached 202 is Yes 206, Complete protocol 208 and End 210. The determination of the optimum will be based upon the response of the physiological and neurological variables to changes to the independent/control variables. By way of example only, if the goal is to reduce blood pressure, adjustments/perturbations are made to performance variables (Table 4) and blood pressure monitored. By mapping the response surface of blood pressure to performance variables, an optimal set of one or more performance variables may be found.

At Reference 194, Manually evaluate physiological and neurological variables and manually adjust control variables 212. (See FIG. 1 and Table 4.) If Optimum reached? 214 is No 216, loop back to Manually evaluate physiological and neurological variables and manually adjust control variables 212. Adjustments may be based upon, for example, perturbing an Independent/Control Variable (Table 4) and check the effects on related Dependent Variables. If Optimum reached 214 is Yes 218, Complete protocol 208 and End 222. As with the automated loop, the determination of the optimum will be based upon the response of the physiological and neurological variables to changes to the independent/control variables.

For example, to initialize a fibromyalgia session, the galvanic skin response (GSR) is measured within the concha 150 (FIG. 4) of the ear 106 to detect pathologic points. The concha 150 is then stimulated on detected points with, for example, near infrared light at about 5 mW on a 5 mm diameter target point 132 at a frequency of about 4.56 Hz for about 10 minutes. Ten minutes after the first stimulation, GSR is measured and pathologic points treated again for a further 10 minutes. The session is then ended. Treatment may continue about every 15 days for six months.

As a further example, for hypotension, thumb 152, hypothalamus 158, sympathetic 154, and liver 156 (FIG. 4) are stimulated bilaterally in that order for one minute each with near infrared light at about 5 mW for 12 minutes and repeated weekly. The biometric variable of interest would be systemic blood pressure.

As a further example, for shoulder pain, the ipsilateral ear is examined for GSR in the region of the following points: shoulder 162, maxilla 164, trigeminal zone 168, eye 166, Point O' 160, and Point Zero 144 (FIG. 4). A 5 mW blue laser light is used operated at 26.5 Hz for 5 minutes. Subsequently, using the same control settings, the following points are stimulated for five minutes: stellate ganglion 170 and maxilla 164. The session is ended with another five minutes with the laser 102 placed over the greatest pain on the shoulder.

Figure 6:
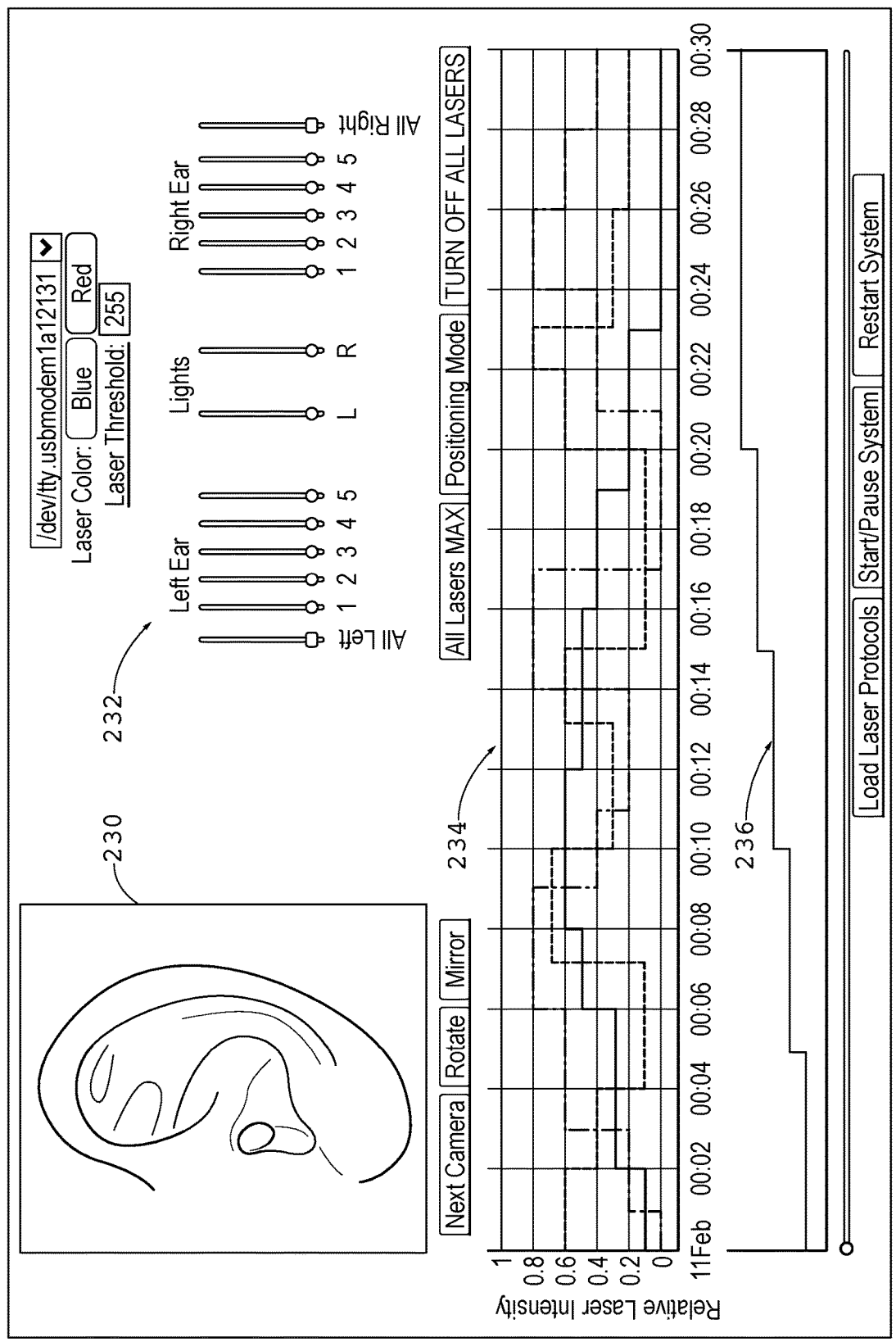
FIG. 6 is an exemplary screenshot of the graphical user interface during a photonic stimulation session.

Turning now to FIG. 6, an exemplary screen shot is shown of the command station 124. At the upper left is a view as seen from the imaging camera 136 (FIG. 3) which can show where the laser beam 130 is shining or where various target points or fiducial marks 132 are found. To the right are mouse or touch screen controls for the various lasers 102 being used. A real-time graph 234 shows, for example, the intensity of the lasers 102 during the session. Finally, at the bottom, the general protocol 236 is shown.

While certain preferred embodiments of the present invention have been disclosed in detail, it is to be understood that various modifications may be adopted without departing from the spirit of the invention or scope of the following claims.

The invention claimed is:

1. An apparatus for photonic physiological stimulation of at least one target point on a subject, the apparatus comprising:
    a housing adapted to be positioned over the at least one target point;
    at least one light source selected from the group consisting of laser, light-emitting diode, and combinations thereof, the at least one light source positioned on the housing whereby light from the light source is focusable onto the at least one target point;
    at least one sensor, the at least one sensor in sensory communication with the subject, the sensor adapted to sense at least one physiological or neurological status of the subject, the sensor further adapted to output the at least one physiological or neurological status;
    a driver, the driver operably connected to the at least one light source, the driver capable of powering and controlling the at least one light source; and
    a command module, the command module operably connected to the driver and operably connected to the sensor, the command module adapted to:
        (a) control at least one performance variable of the at least one light source, the at least one performance variable selected from the group consisting of light wavelength, power, power density, voltage, current, pulse pattern, pulse frequency, beam spot diameter, angle of incidence, and combinations thereof;
        (b) receive at least one status output from the sensor;
        (c) adjust at least one performance variable of at least one laser light;
        (d) subsequent to adjusting at least one performance variable (c), evaluate any change in the status output;

(e) subsequent to evaluating any change in the status output (d), determine if the status output is optimized; and
(f) adjust at least one performance variable of at least one laser light (c) if the status output is not optimized.

2. The apparatus of claim 1, further comprising a further housing, wherein each housing is cup-shaped, each housing adapted to fit the concave portion of the housing over an ear of the subject.

3. The apparatus of claim 1, wherein at least one of the at least one light sources is a laser.

4. The apparatus of claim 3, wherein the laser is capable of emitting light having a wavelength of between about 390 nm and about 700 nm.

5. The apparatus of claim 1, wherein the at least one physiological or neurological status is selected from the group consisting of blood pressure, blood flow, pulse, heart rate variability, blood oxygen saturation, electromyocardiographic response, respiration rate, respiration pattern, galvanic skin response, pupil dilation, trabecular-ciliary process distance, magnetic resonance imaging, brain waves, physical movements, muscle tension, self reporting, and combinations thereof.

6. The apparatus of claim 1, wherein the at least one performance variable is selected from the group consisting of light wavelength, power, power density, voltage, current, pulse pattern, pulse frequency, beam spot diameter, angle of incidence, and combinations thereof.

7. A method for the photonic physiological stimulation of at least one target point on a subject, comprising the steps of:
(a) placing a housing over at least one target point, the housing comprising at least one light source selected from the group consisting of laser, light-emitting diode, and combinations thereof, the light source positioned on the housing whereby light from the light source is focusable onto the target point;
(b) placing at least one sensor in sensory communication with the subject, the sensor adapted to sense at least one physiological or neurological status of the subject, the sensor further adapted to output the status;
(c) energizing the light source at the target point at minimum power and beam spot;
(d) noting the sensor output;
(e) modifying at least one performance variable of the light source;
(f) noting the sensor output;
(g) comparing the sensor output noted in Step (e) with the sensor output noted in Step (f);
(h) returning to Step (e) if the sensor output noted in Step (f) has not reached an optimum.

8. The method of claim 7, wherein the physiological or neurological status is selected from the group consisting of blood pressure, blood flow, pulse, heart rate variability, blood oxygen saturation, electromyocardiographic response, respiration rate, respiration pattern, galvanic skin response, pupil dilation, trabecular-ciliary process distance, magnetic resonance imaging, brain waves, physical movements, muscle tension, self reporting, and combinations thereof.

9. The method of claim 7, wherein the at least one performance variable is selected from the group consisting of light wavelength, power, power density, voltage, current, pulse pattern, pulse frequency, beam spot diameter, angle of incidence, and combinations thereof.

10. A method of physiologically and neurologically stimulating target points on the outer ear of a subject, the method comprising the steps of:
(a) mounting the concave portion of a cup-shaped housing over each ear of the subject, each housing comprising:
a plurality of laser lights positioned at least partially within the concave portion, each laser light mounted to be aimed and focused on a target point on the outer ear, each laser light in operable communication with a driver; and
a video camera positioned at least partially within the concave portion, each video camera mounted to view the outer ear and a beam spot produced by each laser light, the video camera in operable communication with the driver and in operable communication with a command module;
(b) placing at least one sensor in sensory communication with the subject, the sensor in operable communication with the command module, the sensor adapted to sense at least one physiological or neurological status of the subject, the sensor further adapted to output the at least one physiological or neurological status to the command module;
(c) initiating the command module to energize the laser lights at minimum power and beam spot onto the surface of the outer ear;
(d) initiating the command module to adjust laser targeting onto initial target points;
(e) initiating the command module to adjust at least one performance variable of at least one laser light;
(f) initiating the command module to compare a sensor output from before Step (e) to the sensor output from after Step (e); and
(g) initiating the command module to determine if an optimum level of sensor output has been achieved.

* * * * *